United States Patent
Sibal

(10) Patent No.: US 11,377,401 B2
(45) Date of Patent: Jul. 5, 2022

(54) EFFICIENCY OF A GAS CONDITIONING SYSTEM VIA HYDRATE INHIBITOR INJECTION

(71) Applicant: EXXONMOBIL UPSTREAM RESEARCH COMPANY, Spring, TX (US)

(72) Inventor: Paul W. Sibal, The Woodlands, TX (US)

(73) Assignee: ExxonMobil Technology and Engineering Company, Annandale, NJ (US)

(*) Notice: Subject to any disclaimer, the term of this patent is extended or adjusted under 35 U.S.C. 154(b) by 295 days.

(21) Appl. No.: 16/514,491

(22) Filed: Jul. 17, 2019

(65) Prior Publication Data

US 2020/0048168 A1 Feb. 13, 2020

Related U.S. Application Data

(60) Provisional application No. 62/717,410, filed on Aug. 10, 2018.

(51) Int. Cl.
| | |
|---|---|
| *C07C 7/00* | (2006.01) |
| *B01D 53/00* | (2006.01) |
| *B01D 53/14* | (2006.01) |
| *B01D 53/64* | (2006.01) |
| *C07C 7/11* | (2006.01) |
| *C07C 7/20* | (2006.01) |

(52) U.S. Cl.
CPC ............ *C07C 7/005* (2013.01); *B01D 53/002* (2013.01); *B01D 53/1456* (2013.01); *B01D 53/64* (2013.01); *C07C 7/11* (2013.01); *C07C 7/20* (2013.01); *B01D 2257/602* (2013.01); *B01D 2257/80* (2013.01)

(58) Field of Classification Search
CPC .... C07C 7/00; C07C 7/11; C07C 7/20; C07C 7/005; B01D 53/14; B01D 53/64; B01D 53/00
See application file for complete search history.

(56) References Cited

U.S. PATENT DOCUMENTS 2,910,139 A * 10/1959 Matyear, Jr. ........... B01D 53/26
585/650
7,152,431 B2 12/2006 Amin et al. .................... 62/637
(Continued)

*Primary Examiner* — Youngsul Jeong
(74) *Attorney, Agent, or Firm* — Vorys, Sater, Seymour and Pease LLP

(57) ABSTRACT

A gas conditioning system is described herein. The system includes a slug catcher configured to separate a hydrocarbon feed stream into a liquid stream and a gas stream, and a first hydrate inhibitor injection unit configured to lower a hydrate formation temperature of the gas stream using a first hydrate inhibitor. The system includes a pressure reduction unit, a first separation unit configured to remove a first liquid stream including the first hydrate inhibitor from the gas stream, a mercury removal unit, and an acid gas removal unit. The system also includes a second hydrate inhibitor injection unit configured to further lower the hydrate formation temperature of the gas stream using a second hydrate inhibitor, a cooling unit, a second separation unit configured to remove a second liquid stream including the second hydrate inhibitor from the gas stream, and a dehydration unit configured to produce a final treated gas stream.

6 Claims, 7 Drawing Sheets

(56) References Cited

U.S. PATENT DOCUMENTS

| | | |
|---|---|---|
| 7,947,121 B2 | 5/2011 | Bras et al. |
| 9,950,293 B2 | 4/2018 | Kaasa et al. |
| 10,130,897 B2 | 11/2018 | Grave et al. |
| 2007/0193303 A1 | 8/2007 | Hawrysz et al. |
| 2012/0079852 A1* | 4/2012 | Northrop ............... F25J 3/0233 62/620 |
| 2016/0102262 A1* | 4/2016 | Moore .................... C10L 3/106 62/633 |

* cited by examiner

100

200

400

EFFICIENCY OF A GAS CONDITIONING SYSTEM VIA HYDRATE INHIBITOR INJECTION

CROSS REFERENCE TO RELATED APPLICATIONS

This application claims the priority benefit of U.S. Provisional Patent Application No. 62/717,410 filed Aug. 10, 2018, entitled IMPROVING THE EFFICIENCY OF A GAS CONDITIONING SYSTEM VIA HYDRATE INHIBITOR INJECTION.

FIELD

The present techniques provide for improving the efficiency of a gas conditioning system via hydrate inhibitor injection. More specifically, the present techniques provide for the use of one or more hydrate inhibitor injection units within a gas conditioning system to improve the efficiency of the gas conditioning system.

BACKGROUND

This section is intended to introduce various aspects of the art, which may be associated with exemplary embodiments of the present techniques. This discussion is believed to assist in providing a framework to facilitate a better understanding of particular aspects of the present techniques. Accordingly, it should be understood that this section should be read in this light, and not necessarily as admissions of prior art.

Large volumes of natural gas are located in remote areas of the world. This natural gas has significant value if it can be economically transported to market. When a natural gas reserve is located in reasonable proximity to a market and the terrain and political climate between the two locations permit, and suitable commercial terms deem gas sales viable, the natural gas is typically produced and then transported to market through submerged and/or land-based pipelines. However, when the natural gas is produced in locations where laying a pipeline is infeasible or politically or economically prohibitive, other techniques must be used for transporting the gas to market.

A commonly used technique for non-pipeline transport of natural gas involves liquefying the natural gas by cooling and condensing the natural gas to a liquid state within a gas processing facility at or near the production site. The liquefied natural gas (LNG) may then be transported to market in specially-designed storage tanks aboard transport vessels. Moreover, in some cases, it may be desirable to recover natural gas liquids (NGLs) from the natural gas within the gas processing facility. NGLs are liquid hydrocarbons including ethane and heavier, or propane and heavier, either mixed or fractionated into separate products.

In conventional gas processing facilities where the recovery of NGLs and/or the production of LNG is part of the overall plant design objective, feedstock into the facility is typically taken from either a pipeline that transmits sales-quality natural gas, or from one or more pipelines that connect dedicated producing oil and/or gas fields to the gas processing facility. The gas processing facility can be located nearby or distant to the sales gas pipeline or producing field(s). Further, the gas processing facility can be located on land, on a ship-shaped or other floating support structure, or on some other support structure such as a bottom-founded offshore platform.

For operations in which there is no sales gas pipeline between the producing fields that provide feedstock to a gas processing facility, the hydrocarbon feed stream, i.e., the fluids leaving one or more wells drilled into an oil and/or gas resource, is typically cooled before it flows through separation facilities located at or near the producing wells. In that separation step, liquid water and liquid hydrocarbons are removed from the hydrocarbon feed stream. The water removed in that separation step is cleaned up for safe and environmentally-sound disposal. The separation step also produces a predominantly gas stream, which can be dehydrated, typically using a system that employs a hygroscopic liquid such as triethylene glycol to absorb most of the water vapor contained in the gas stream. The dehydrated gas and liquid hydrocarbons can then be pipelined separately or recombined to flow in a single, multiphase pipeline. The resulting pipeline transport system, co-mingled in a single pipeline or using separate gas and liquid pipelines, is generally referred to as a "dry gas pipeline system."

Dehydrating the natural gas stream before it enters the pipeline helps to reduce the potential for corrosion, which might result from the presence of acid gas components, such as carbon dioxide ($CO_2$) and hydrogen sulfide ($H_2S$), and liquid water in the pipeline. In addition, dehydrating the natural gas stream helps to prevent hydrate formation in the pipeline. Hydrates are solid, ice-like compounds that form from water and low molecular weight hydrocarbons or other wellstream or sales gas components, e.g. $CO_2$, $H_2S$, and mercaptans, under conditions of reduced temperature and elevated pressure. More specifically, hydrates are solid crystalline products that form when water encages hydrocarbons and other hydrate-forming molecules, such as methane. In certain circumstances, hydrates may form at temperatures well above the freezing point of water. As an example, for methane in the presence of liquid water, the initial hydrate formation temperature ranges between 32° F. (0° C.) and 77° F. (25° C.), which is dependent upon the specific pressure. Similar to ice formed from water, hydrates from the gas stream may plug pipelines and other processing equipment, resulting in shutdowns and other operational problems.

In other operations where there is no sales gas pipeline between the producing fields and the gas processing facility, the full undehydrated hydrocarbon feed stream can be transported through a pipeline to the gas processing facility for the recovery of NGLs and/or the production of LNG. This is typically called a "wet gas pipeline system." In such wet gas pipeline systems, a hydrate inhibitor, such as monoethylene glycol (MEG), may be injected into the hydrocarbon feed stream at the pipeline inlet to prevent hydrate formation in the pipeline. Moreover, the hydrocarbon feed stream may be sent through a gas conditioning system before it is sent to the gas processing facility. The gas conditioning system may condition the hydrocarbon feed stream for cryogenic processing by removing impurities, such as water, acid gases, and mercury, from the hydrocarbon feed stream.

According to current techniques, the temperature of the hydrocarbon stream must be carefully monitored and controlled as it flows through the gas conditioning system to ensure that hydrates do not form within the system, and to protect certain aspects of the gas conditioning system from contact with liquid hydrocarbons. This is typically accomplished by operating heating and cooling units within the gas conditioning system such that the temperature of the hydrocarbon stream remains sufficiently above the hydrate formation temperature of the hydrocarbon stream and the hydrocarbon dew point of the hydrocarbon stream. However, such temperature constraints and heat input requirements significantly limit the efficiency of the overall system.

SUMMARY

An exemplary embodiment provides a gas conditioning system. The gas conditioning system includes a slug catcher configured to separate a hydrocarbon feed stream into a liquid stream and a gas stream, and a first hydrate inhibitor injection unit configured to inject a first hydrate inhibitor into the gas stream such that the hydrate formation temperature of the gas stream is altered from a first hydrate formation temperature to a second, lowered hydrate formation temperature. The gas conditioning system also includes a pressure reduction unit configured to reduce the pressure of the gas stream, a first separation unit configured to remove a first liquid stream including condensed water combined with the first hydrate inhibitor and condensed hydrocarbons from the gas stream, and a mercury removal unit configured to remove mercury from the gas stream. The gas conditioning system also includes an acid gas removal unit configured to remove acid gases from the gas stream, and a second hydrate inhibitor injection unit configured to inject a second hydrate inhibitor into the gas stream such that the hydrate formation temperature of the gas stream is altered from a third hydrate formation temperature to a fourth, lowered hydrate formation temperature. The gas conditioning system further includes a cooling unit configured to reduce the temperature of the gas stream, a second separation unit configured to remove a second liquid stream including additional condensed water combined with the second hydrate inhibitor and additional condensed hydrocarbons from the gas stream, and a dehydration unit configured to remove residual water from the gas stream, producing a final treated gas stream.

Another exemplary embodiment provides a method for improving the efficiency of a gas conditioning system via hydrate inhibitor injection. The method includes separating a hydrocarbon feed stream into a liquid stream and a gas stream within a slug catcher, and injecting a first hydrate inhibitor into the gas stream within a first hydrate inhibitor injection unit such that the hydrate formation temperature of the gas stream is altered from a first hydrate formation temperature to a second, lowered hydrate formation temperature. The method also includes reducing the pressure of the gas stream within a pressure reduction unit, removing a first liquid stream including condensed water combined with the first hydrate inhibitor and condensed hydrocarbons from the gas stream within a first separation unit, and removing mercury from the gas stream within a mercury removal unit. The method also includes removing acid gases from the gas stream within an acid gas removal unit, and injecting a second hydrate inhibitor into the gas stream within a second hydrate inhibitor injection unit such that the hydrate formation temperature of the gas stream is altered from a third hydrate formation temperature to a fourth, lowered hydrate formation temperature. The method further includes reducing the temperature of the gas stream within a cooling unit, removing a second liquid stream including additional condensed water combined with the second hydrate inhibitor and additional condensed hydrocarbons from the gas stream within a second separation unit, and removing residual water from the gas stream within a dehydration unit, producing a final treated gas stream.

Another exemplary embodiment provides a method for injecting a hydrate inhibitor into a gas stream prior to reducing the pressure of the gas stream. The method includes separating a hydrocarbon feed stream into a liquid stream and a gas stream within a slug catcher and injecting a hydrate inhibitor into the gas stream within a hydrate inhibitor injection unit. The method also includes mixing the hydrate inhibitor with the gas stream within the hydrate inhibitor injection unit such that the hydrate inhibitor lowers the hydrate formation temperature of the gas stream, and reducing the pressure of the gas stream within a pressure reduction unit.

Another exemplary embodiment provides a method for injecting a hydrate inhibitor into a gas stream prior to reducing the temperature of the gas stream. The method includes removing acid gases from a gas stream within an acid gas removal unit and injecting a hydrate inhibitor into the gas stream within a hydrate inhibitor injection unit. The method also includes mixing the hydrate inhibitor with the gas stream within the hydrate inhibitor injection unit such that the hydrate inhibitor lowers the hydrate formation temperature of the gas stream, and reducing the temperature of the gas stream within a cooling unit.

DESCRIPTION OF THE DRAWINGS

The advantages of the present techniques are better understood by referring to the following detailed description and the attached drawings, in which.

DETAILED DESCRIPTION

Figure 1A:
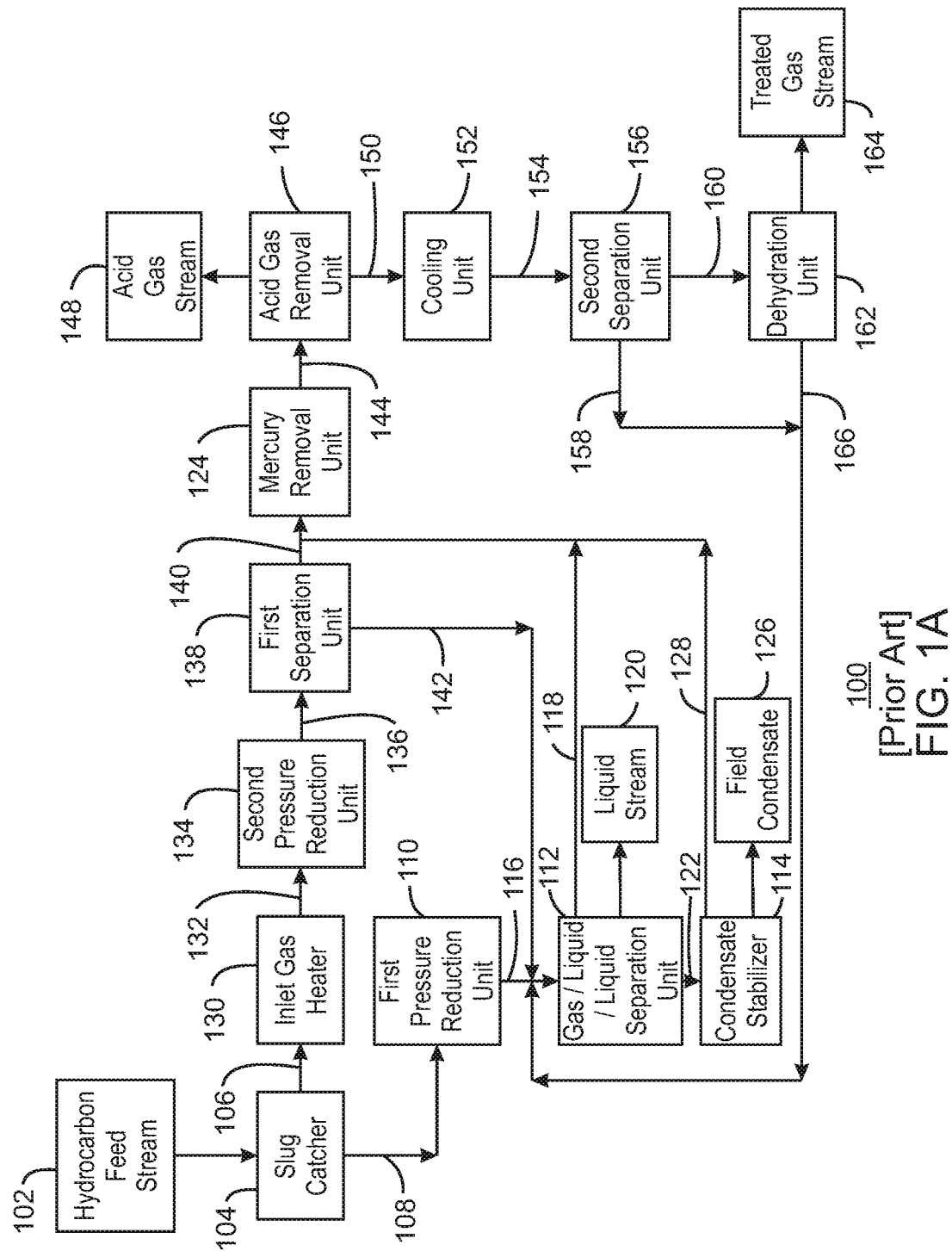
FIG. 1A is a process flow diagram of a gas conditioning system.

In the following detailed description section, specific embodiments of the present techniques are described. However, to the extent that the following description is specific to a particular embodiment or a particular use of the present techniques, this is intended to be for exemplary purposes only and simply provides a description of the exemplary embodiments. Accordingly, the techniques are not limited to the specific embodiments described below, but rather, include all alternatives, modifications, and equivalents falling within the true spirit and scope of the appended claims.

At the outset, for ease of reference, certain terms used in this application and their meanings as used in this context are set forth. To the extent a term used herein is not defined below, it should be given the broadest definition persons in the pertinent art have given that term as reflected in at least one printed publication or issued patent. Further, the present techniques are not limited by the usage of the terms shown below, as all equivalents, synonyms, new developments, and terms or techniques that serve the same or a similar purpose are considered to be within the scope of the present claims.

"Acid gas" refers to any gas that dissolves in water, producing an acidic solution. Non-limiting examples of acid gases include hydrogen sulfide ($H_2S$), carbon dioxide ($CO_2$), sulfur dioxide ($SO_2$), carbon disulfide ($CS_2$), carbonyl sulfide (COS), mercaptans, or mixtures thereof.

As used herein, the term "co-current contacting device" or "co-current contactor" means a vessel that receives (i) a stream of gas and (ii) a separate stream of solvent in such a manner that the gas stream and the solvent stream contact one another while flowing in generally the same direction within the contacting device.

The term "co-currently" refers to the internal arrangement of process streams within a unit operation that can be divided into several sub-sections by which the process streams flow in the same direction.

As used herein, a "column" is a separation vessel in which a counter-current flow is used to isolate materials on the basis of differing properties. In an absorbent column, a physical or chemical solvent is injected into the top, while a mixture of gases to be separated is flowed through the bottom. As the gases flow upwards through the falling stream of absorbent, one or more gas species are preferentially absorbed, lowering the concentration of the gas species in the vapor stream exiting the top of the column. A portion of the vapor stream may be condensed and pumped back into the top of the column as a reflux stream, which can be used to enhance the separation and purity of the overhead product. A bulk liquid stripper is related to a fractionation column. However, a bulk liquid stripper functions without the use of a reflux stream and, thus, cannot produce a high-purity overhead product.

In a "distillation column," liquid and vapor phases are counter-currently contacted to effect separation of a fluid mixture based on boiling points or vapor pressure differences. The higher vapor pressure, or lower boiling, component(s) will tend to concentrate in the vapor phase whereas the lower vapor pressure, or higher boiling, component(s) will tend to concentrate in the liquid phase. Cryogenic separation is a separation process carried out, at least in part, at temperatures at or below 150 degrees Kelvin (K). To enhance the separation, both types of columns may use a series of vertically spaced trays or plates mounted within the column and/or packing elements such as structured or random packing. Columns may often have a recirculated stream at the base to provide heat energy for boiling the fluids, called reboiling.

The term "dehydrated gas stream" refers to a natural gas stream that has undergone a dehydration process. Typically, the dehydrated gas stream has a water content of less than 7 pounds of water per million standard cubic feet for pipeline applications (roughly 150 ppm), and preferably less than 1 ppm in cryogenic/LNG applications. Any suitable process for dehydrating the natural gas stream can be used. Typical examples of suitable dehydration processes include, but are not limited to, treatment of the natural gas stream with molecular sieves or dehydration using glycol or methanol. Alternatively, the natural gas stream can be dehydrated by formation of methane hydrates; for example, using a dehydration process as described in WO2004/070297.

As used herein, the term "dehydration" refers to the pre-treatment of a raw feed gas stream to partially or completely remove water and, optionally, some heavy hydrocarbons. This can be accomplished by means of a pre-cooling cycle, against an external cooling loop or a cold internal process stream, for example. Water may also be removed by means of pre-treatment with molecular sieves, e.g. zeolites, or silica gel or alumina oxide or other drying agents. Water may also be removed by means of washing with glycol, monoethylene glycol (MEG), diethylene glycol (DEG) or triethylene glycol (TEG), or glycerol. The amount of water in the gas feed stream is suitably less than 1 vol. %, preferably less than 0.1 vol. %, more preferably less than 0.01 vol. %.

The term "distillation," or "fractionation," refers to the process of physically separating physical or chemical components into a vapor phase and a liquid phase based on differences in the components' boiling points and vapor pressures at specified temperatures and pressures. Distillation is typically performed in a "distillation column," which includes a series of vertically spaced plates, structured packing, or random packing. A feed stream enters the distillation column at a mid-point, dividing the distillation column into two sections. The top section may be referred to as the rectification section, and the bottom section may be referred to as the stripping section. Condensation and vaporization occur on each plate, or in each increment of structured or random packing, causing lower boiling point components to rise to the top of the distillation column and higher boiling point components to fall to the bottom. A re-boiler is located at the base of the distillation column to add thermal energy. The "bottoms" product is removed from the base of the distillation column. A condenser can be located at the top of the distillation column to fully or partially condense the product emanating from the top of the distillation column, which is called the distillate. A reflux pump is used to maintain liquid flow in the rectification section of the distillation column by pumping a portion of the distillate back into the distillation column.

As used herein, the term "fluid" refers to gases, liquids, and combinations of gases and liquids, as well as to combinations of gases and solids, and combinations of liquids and solids.

The term "gas" is used interchangeably with "vapor," and is defined as a substance or mixture of substances in the gaseous state as distinguished from the liquid or solid state. Likewise, the term "liquid" means a substance or mixture of substances in the liquid state as distinguished from the gas or solid state.

As used herein, "heavy hydrocarbons" refers to hydrocarbons having more than one carbon atom. Principal examples include ethane, propane, and butane. Other examples include pentane and aromatics.

The term "hydrate-forming constituent" refers to a compound or molecule in petroleum fluids, including natural gas, that forms hydrates at elevated pressures and/or reduced temperatures. A "hydrate" is a crystalline solid which looks like ice and forms when water molecules form a cage-like structure around a "hydrate-forming constituent." Illustrative hydrate-forming constituents include, but are not limited to, hydrocarbons such as methane, ethane, propane, isobutane, butane, neopentane, ethylene, propylene, isobutylene, cyclopropane, cyclobutane, cyclopentane, cyclohexane, and benzene. Hydrate-forming constituents can also include non-hydrocarbons, such as oxygen, nitrogen, hydrogen sulfide, mercaptans, carbon dioxide, sulfur dioxide, and chlorine, for example.

As used herein, the term "hydrate inhibitor" refers to a liquid that is capable of lowering the "hydrate formation temperature" of a hydrocarbon stream. The "hydrate formation temperature" is the temperature at which the hydrocarbon stream begins to form hydrates. In various embodiments, the hydrate inhibitor includes glycol. MEG, DEG, TEG, or glycerol, for example.

A "hydrocarbon" is an organic compound that primarily includes the elements hydrogen and carbon, although nitrogen, sulfur, oxygen, metals, or any number of other elements may be present in small amounts. As used herein, the term "hydrocarbon" generally refers to components found in natural gas, oil, bitumen, or chemical processing facilities. Moreover, the term "hydrocarbon" may refer to components found in raw natural gas, such as $CH_4$, $C_2H_2$, $C_2H_4$, $C_2H_6$, $C_3$ isomers, $C_4$ isomers, benzene, and the like.

The term "hydrocarbon feed stream" refers to a hydrocarbon composition prior to any treatment other than that required to enable pipeline transport, such as treatment including cleaning, dehydration and/or scrubbing. The term also refers to any composition having been partly, substantially or wholly treated for the reduction and/or removal of compounds or substances, including, but not limited to, sulfur, sulfur compounds, carbon dioxide, water, mercury, and $C_{2+}$ hydrocarbons.

The term "liquefied gas" refers to any gas that can be stored or transferred in a liquid phase. For example, the term "liquefied gas" includes, but is not limited to, liquefied natural gas (LNG), liquefied petroleum gas (LPG), liquefied energy gas (LEG), liquefied ethylene, natural gas liquids (NGLs), liquefied methane, liquefied ethane, liquefied propane, liquefied butane, liquefied ammonia, combinations thereof, and derivatives thereof. For simplicity and ease of description, the embodiments will be further described with reference to LNG and/or NGLs.

"Liquefied natural gas" (LNG) is natural gas generally known to include a high percentage of methane. However, LNG may also include other compounds. The other elements or compounds may include, but are not limited to, ethane, propane, butane, carbon dioxide, nitrogen, helium, hydrogen sulfide, or combinations thereof.

The term "liquid solvent" refers to a fluid in substantially liquid phase that preferentially absorbs one component over another, with or without the formation of reversible chemical bonds. For example, a liquid solvent may preferentially absorb an acid gas through formation of reversible chemical bonds, thereby removing or "scrubbing" at least a portion of the acid gas component from a gas stream. Moreover, a liquid solvent may preferentially absorb one acid gas over another.

"Natural gas" refers to a multi-component gas obtained from a crude oil well or from a subterranean gas-bearing formation. The composition and pressure of natural gas can vary significantly. A typical natural gas stream contains methane ($CH_4$) as a major component, i.e., greater than 50 mol % of the natural gas stream is methane, although some natural gas streams resulting from oil production can have a lower methane content. The natural gas stream can also contain ethane ($C_2H_6$), higher molecular weight hydrocarbons (e.g., $C_3$-$C_{20}$ hydrocarbons), acid gases (e.g., $CO_2$, $H_2S$, or mercaptans), or any combinations thereof. The natural gas can also contain minor amounts of contaminants such as water, nitrogen, wax, crude oil, or any combinations thereof. The natural gas stream may be substantially purified prior to use in embodiments described herein, so as to remove compounds that may act as poisons.

The term "natural gas liquids" (NGLs) refers to mixtures of hydrocarbons whose components are, for example, typically ethane and heavier. Some examples of hydrocarbon components of NGL streams include ethane, propane, butane, and pentane isomers, benzene, toluene, other aromatic molecules, and possibly small amounts of methane, $CO_2$, and other components.

As used herein, the term "slug" refers to a volume of liquid that is entrained within natural gas production fluids and is often of a higher density than the production fluids, for example, a liquid zone carried along by gas flow in a pipeline. Slugs may affect the flow characteristics of the production fluids. In addition, slugs exiting a pipeline may overload the gas-liquid handling capacity of the subsea, topsides, or onshore processing facility at the pipeline outlet. Thus, a "slug catcher" may be used to dampen or remove the slugs from the production fluids before the production fluids enter the export pipelines or other gas processing facilities.

"Solvent" refers to a substance capable at least in part of dissolving, absorbing, or dispersing other substances, such as to provide or form a solution. The solvent may be polar, nonpolar, neutral, protic, aprotic, or the like. The solvent may include any suitable element, molecule, or compound, such as methanol, ethanol, propanol, glycols, ethers, ketones, other alcohols, amines, salt solutions, or the like. The solvent may include physical solvents, chemical solvents, or the like. The solvent may operate by any suitable mechanism, such as physical absorption, chemical absorption, chemisorption, physisorption, adsorption, pressure swing adsorption, temperature swing adsorption, or the like.

"Substantial" when used in reference to a quantity or amount of a material, or a specific characteristic thereof, refers to an amount that is sufficient to provide an effect that the material or characteristic was intended to provide. The exact degree of deviation allowable may depend, in some cases, on the specific context.

The term "sweetened gas stream" refers to a fluid stream in a substantially gaseous phase that has had at least a portion of acid gas components removed.

Overview

The present techniques provide for improving the efficiency of a gas conditioning system via hydrate inhibitor injection. More specifically, the present techniques provide for the use of hydrate inhibitor injection units within a gas conditioning system to improve the efficiency of the gas conditioning system. According to embodiments described herein, hydrate inhibitor injection units are strategically placed within a gas conditioning system such that the load on heating units within the gas conditioning system is reduced or, in some cases, eliminated, and the load on specific cooling units can be increased to improve process thermal and capital efficiency. The use of such hydrate inhibitor injections units prevents hydrate formation within the gas conditioning system and enables additional liquid hydrocarbon condensation within the gas conditioning system, while reducing the capital and operating costs of the system inclusive of downstream equipment intended for NGL recovery and/or LNG production.

Gas Conditioning System

FIG. 1A is a process flow diagram of a gas conditioning system 100. In various embodiments, the gas conditioning system 100 is used to condition a hydrocarbon feed stream 102 for LNG production and/or NGL recovery within a downstream gas processing facility (not shown). The hydrocarbon feed stream 102 may be sent from the producing field(s) to the gas conditioning system through a wet gas pipeline system or a dry gas pipeline system.

As shown in FIG. 1A, the hydrocarbon feed stream 102 may be sent into a slug catcher 104 within the gas conditioning system 100. The slug catcher 104 may separate the hydrocarbon feed stream 102 into a gas stream 106 and a liquid stream 108. In some embodiments, the slug catcher 104 is a finger-type slug catcher including multiple parallel lengths of near-horizontal pipe that are manifolded together and sloped downward from the inlet and again manifolded together at the low elevation point, thereby creating a liquid collection service that can receive and contain the liquid "slugs." These slugs are intermittent periods of above-normal liquid flow out of the pipeline. The liquid inventory thereby contained in the slug catcher can then be processed at a relatively constant rate. The slug catcher 104 may also be designed to facilitate gas disengagement from the liquids through another set of piping manifolds located on the inlet end and the top of the slug catcher 104, and produce a relatively constant rate of gas flow to downstream equipment. Moreover, it is to be understood that, while the term "slug catcher" is used herein, the slug catcher 104 shown in FIG. 1A may be replaced with any type of separation device that is configured to separate the hydrocarbon feed stream into the gas stream 106 and the liquid stream 108. For example, in some embodiments, the slug catcher 104 is replaced with a conventional horizontal or vertical pressure vessel designed for gas and liquid separation.

In addition, while FIG. 1A shows a single liquid stream 108 leaving the slug catcher 104, it is to be understood that, for wet gas pipelines, two liquid phases may be present, and the slug catcher 104 may produce two separate liquid streams, one predominantly hydrocarbons and one containing the majority of the liquid water. In embodiments in which the hydrocarbon feed stream 102 is received from a wet gas pipeline, the liquid phase containing the majority of the condensed water may also contain a hydrate inhibitor, e.g. MEG or TEG, along with some dissolved hydrocarbons and entrained liquid hydrocarbon.

The liquid stream 108 exiting the slug catcher 104 may include components that tend to cause freezing and plugging problems in cryogenic processes. Specifically, the liquid stream 108 may include condensed hydrocarbon liquids, often referred to as "field condensate" separated from the gas stream 106 at high pressure, such as 500-1,000 psig or higher, and may contain significant amounts of dissolved methane, ethane, propane, and butanes. For transportation and subsequent use, the liquid stream 108 may be sent through field condensate stabilization equipment. The field condensate stabilization equipment may include a first pressure reduction unit 110, a gas/liquid/liquid separation unit 112, and a condensate stabilizer 114.

The first pressure reduction unit 110 may reduce the pressure of the liquid stream 108, producing a predominately liquid stream 116. The predominately liquid stream 116 may then be flowed into the gas/liquid/liquid separation unit 112. The gas/liquid/liquid separation unit 112 may be configured to separate the predominately liquid stream 116 into an off-gas stream 118, a liquid stream 120 including water or a mixture of water and a hydrate inhibitor (which may be present if the hydrocarbon feed stream 102 traveled through a wet gas pipeline system), and a liquid hydrocarbon stream 122.

The resulting off-gas stream 118 may be compressed within an off-gas compressor unit (not shown) and fed back into the gas conditioning system 100 upstream of a mercury removal unit 124. The liquid stream 120 may be sent to downstream processing equipment (not shown) for disposal or reuse.

The liquid hydrocarbon stream 122 may be flowed into the condensate stabilizer 114. The condensate stabilizer 114 may substantially remove dissolved light hydrocarbons, such as methane, ethane, propane, butanes, and potentially some of the pentanes, to reduce the vapor pressure of the liquid hydrocarbon stream 122 to typically below atmospheric pressure. Removing the light hydrocarbons to lower the vapor pressure may increase the heating value of the resulting field condensate 126 and reduce the potential problems caused by later off-gassing of the light components as the pressure and temperature of the field condensate 126 changes during transport and storage. Once the field condensate 126 is removed within the condensate stabilizer 114, a resulting off gas stream 128 may be compressed within an off-gas compressor unit (not shown) and fed back into the gas conditioning system 100 upstream of the mercury removal unit 124, along with the off-gas stream 118 exiting the gas/liquid/liquid separation unit 112. Moreover, in some embodiments, liquid hydrocarbons condensed within the gas conditioning system 100 are sent to a second condensate stabilization unit (not shown) to produce plant condensate that is separate from the field condensate 126 originating from liquid hydrocarbons removed from the slug catcher 104.

From the slug catcher 104, the gas stream 106 may be flowed through an inlet gas heater 130. The inlet gas heater 130 may heat the gas stream 106 to prevent hydrate formation within the gas conditioning system 100. Hydrates are complexes of water and lighter hydrocarbons that resemble ice and can form at temperatures above the normal freezing point of water. The hydrate formation temperature is generally higher at higher operating pressure. The hydrocarbon feed stream 102 exiting the pipeline, and therefore the gas stream 106 exiting the slug catcher 104, will be essentially at the same temperature as the seawater through which the pipeline traversed, in the case of offshore production, or the same temperature as the ground through which the pipeline traversed. Depending on the pressure drop in the feed gas pipeline, the slug catcher 104 operating temperature can actually be less than that of the surrounding seawater or ground as a result of auto-refrigeration from the Joule Thompson effect. The inlet gas heater 130 is generally required when the hydrocarbon feed stream 102 is sourced from a wet gas pipeline system, because the gas stream 106 exiting the slug catcher 104 in such a design is water saturated. The temperature of the gas stream 106 within the inlet gas heater 130 may be controlled such that the temperature of the resulting heated gas stream 132 remains above the hydrate formation temperature.

The heated gas stream 132 may then be sent through a second pressure reduction unit 134. The second pressure reduction unit 134 may include control valves operated in parallel, with the number of control valves depending on the gas flow rate and the variability of the pipeline outlet gas flow rate. The resulting predominately gas phase stream 136 may then be flowed into a first separation unit 138. The first separation unit 138 may be a conventional or compact horizontal or vertical pressure vessel designed to separate the predominately gas phase stream 136 into a gas stream 140 and a liquid stream 142. The liquid stream 142 may be combined with the predominately liquid stream 116 entering the gas/liquid/liquid separation unit 112.

The gas stream 140 may then be flowed into the mercury removal unit 124. The mercury removal unit 124 may be a pressure vessel that includes a bed of sulfur-impregnated activated carbon granules, although other media can be used for this purpose. The gas stream 140 may flow downward through and over the bed of granules. Any mercury vapor within the gas stream 140 may react with the sulfur, in embodiments in which sulfur-impregnated carbon granules are used, forming a solid that remains on the granules. A resulting mercury-free gas stream 144 may then flow out of the mercury removal unit 124. In some embodiments, the mercury-free gas stream 144 is then sent through a filter separation unit (not shown). The filter separation unit may remove solids, such as dust, that might have been picked up by the mercury-free gas stream 144 within the mercury removal unit 124.

The mercury-free gas stream 144 may then be sent into an acid gas removal unit (AGRU) 146. The AGRU 146 may be any system that is configured to remove acid gases, such as $CO_2$, $H_2S$, and mercaptans (RSH), from the mercury-free gas stream 144. This processing step enables the production of sales gas and/or natural gas products that meet pipeline and sales specifications for $CO_2$ content, $H_2S$ content, and total sulfur content.

In some embodiments, the AGRU 146 includes a conventional absorber column and a regenerator column (not shown) for the purpose of solvent regeneration. In such embodiments, an amine-based solvent, for example, may be injected into the top of an absorber column, while the mercury-free gas stream 144 may be flowed into the bottom of the absorber column. As the mercury-free gas stream 144 flows upward through the falling stream of solvent, the acid gases are absorbed by the solvent, lowering the concentration of acid gases in the gas stream exiting the top of the absorber column.

In other embodiments, the AGRU 146 includes a co-current contacting system (not shown) instead of a counter-current contactor. The co-current contacting system may include a co-current contactor configured to allow the mercury-free gas stream 144 and an amine-based solvent stream, for example, to co-currently flow into the co-current contactor. The co-current contactor may provide for the efficient incorporation of liquid droplets formed from the solvent stream into the mercury-free gas stream 144 such that acid gases within the mercury-free gas stream 144 are entrained within the liquid droplets. The mixture may then be sent through a separation system within the co-current contacting system, which may produce an acid gas stream 148 and a sweetened gas stream 150.

The acid gas stream 148 exiting the AGRU 146 may be composed of acid gases chemically or physically removed from the mercury-free gas 144 by the solvent stream. In some embodiments, this "rich" solvent stream is regenerated within a solvent regeneration unit (not shown) by removing the acids gases from the solvent stream. The resulting "lean" solvent stream may then be reused within the AGRU 146. In some embodiments, a sulfur product is then recovered from the $H_2S$ and mercaptans (if any) by processing the recovered acid gas stream within a sulfur recovery unit (SRU) (not shown). In addition, in some embodiments, the recovered acid gas stream is injected into a subsurface disposal reservoir. Moreover, in some embodiments, the acid gas stream 148 can be vented to the atmosphere, with or without incineration to convert $H_2S$ and/or mercaptans to sulfur oxides prior to release to the atmosphere.

The sweetened gas stream 150 exiting the AGRU 146 may be saturated with water as a result of its contact with the aqueous amine-based solvent stream. Therefore, the sweetened gas stream 150 may not yet be suitable for sales, NGL recovery, or LNG production. Therefore, the sweetened gas stream 150 may be sent through a cooling unit 152. The cooling unit 152 may be configured to condense some of the water (and potentially some of the heavier hydrocarbons) in the sweetened gas stream 150. In some embodiments, the cooling unit 152 cools the sweetened gas stream 150 through cross-heat exchange with a cold product stream or other cold fluid. In other embodiments, the cooling unit 152 cools the sweetened gas stream 150 using a refrigerant. Within the conventional gas conditioning system 100 of FIG. 1A, the extent of cooling in this step is limited to prevent hydrate formation within the equipment. If the operating conditions were to allow hydrates to form, the hydrates would restrict and potentially block the flow of gas to downstream equipment. Such limited cooling is typically accomplished by controlling the temperature of the process gas stream 154 exiting the cooling unit 152 such that the temperature of the process gas stream 154 remains above its hydrate formation temperature of, for example, about 20° C. (68° F.), or higher.

The process gas stream 154 may then be flowed into a second separation unit 156. The second separation unit 156 may be configured to separate the process gas stream 154 into a liquid stream 158 including any condensed water and hydrocarbons and an essentially liquid-free gas stream 160.

The liquid-free gas stream 160 may then be sent through a dehydration unit 162. The dehydration unit 162 may be configured to remove water vapor from the liquid-tree gas stream 160 to prevent hydrate formation in the downstream cryogenic gas processing equipment (not shown). In some embodiments, the dehydration unit 162 is a molecular sieve system including two or more vessels operating in parallel that contain granules of crystalline aluminosilicates, or zeolites, which have a high surface area per unit of mass and an affinity for water vapor. Water vapor may adsorb onto the surface of these molecular sieve granules, producing a final treated gas stream 164 with a very low water content, i.e., on the order of 0.1 parts per million. The adsorption process may be allowed to continue until the molecular sieve in a given vessel approaches saturation, meaning that the molecular sieve has adsorbed nearly all of the water vapor it can without allowing appreciable water vapor to flow downstream, or "break through." At that point, flow may be switched from the used bed of molecular sieve to a fresh bed of molecular sieves. The adsorbed water may be removed from the used bed of molecular sieve through a regeneration process that involves isolating the used bed within the dehydration unit 162 from the typically downward-flowing liquid-free gas stream 160 and flowing hot regeneration gas typically upward through the bed of molecular sieves. The hot, water-laden regeneration gas stream exiting the bed may then be cooled and fed into a gas/liquid separation device (not shown), and a resulting liquid steam 166 may be routed back into the gas conditioning system 100 upstream of the gas/liquid/liquid separation unit 112. Moreover, in various embodiments, the final treated gas stream 164 exiting the gas conditioning system 100 is sent to a downstream gas processing facility (not shown) for LNG production and/or NGL recovery.

In practice, the efficiency of the gas conditioning system 100 of FIG. 1A is limited by the hydrate formation temperature constraints imposed on the system 100. For example, the use of the inlet gas heater 130 to maintain the temperature of the gas stream 106 above its hydrate formation temperature reduces the efficiency of downstream equipment, such as the AGRU 146, and increases the capital and operating costs of the system 100. Moreover, the cooling unit 152 may not be operated at maximum efficiency because the temperature of the sweetened gas stream 150 must also remain above its hydrate formation temperature. Therefore, according to embodiments described herein, hydrate inhibitor injection is utilized to improve the efficiency of the gas conditioning system 100, as described further with respect to FIG. 1B.

Figure 1B:
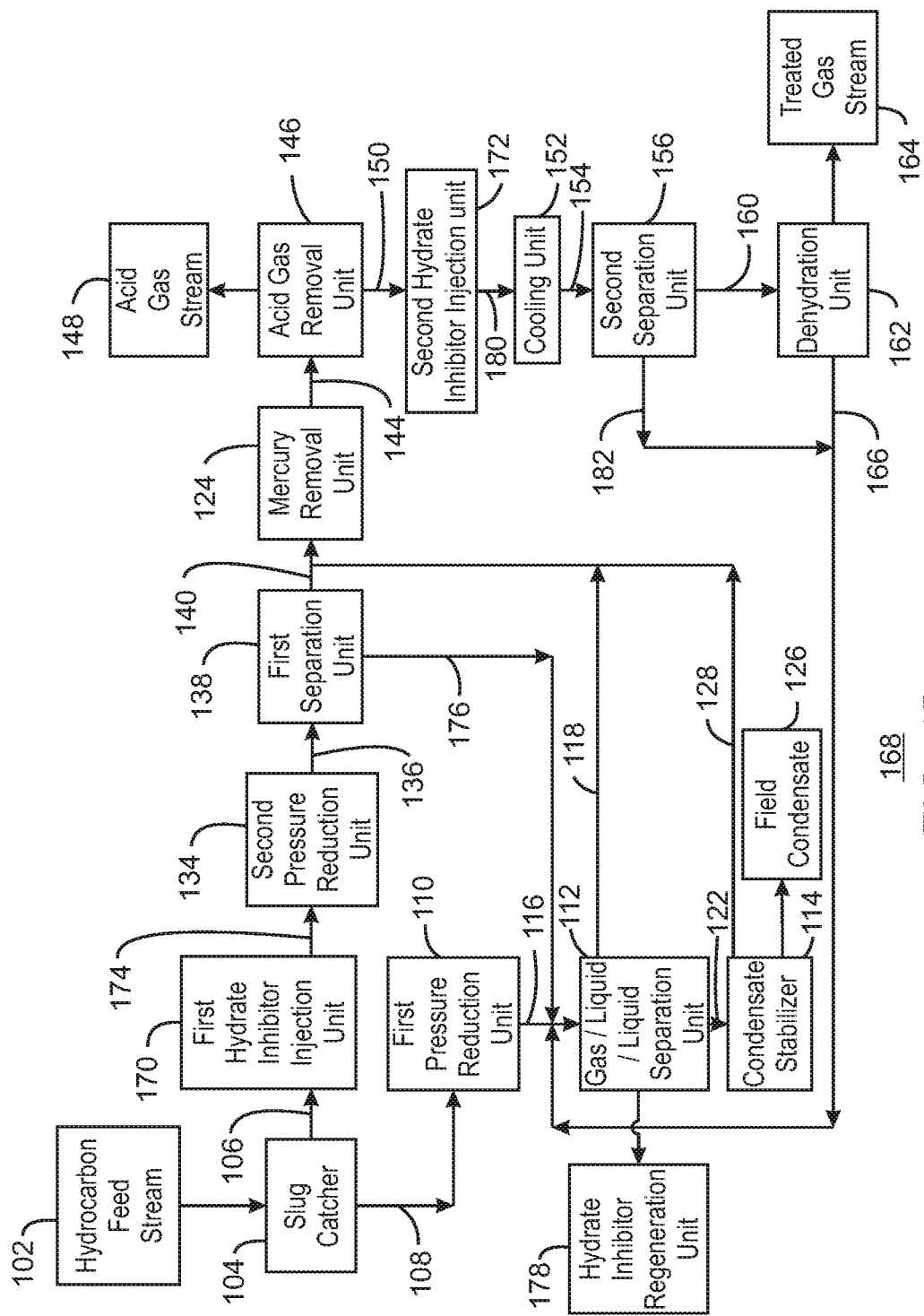
FIG. 1B is a process flow diagram of a gas conditioning system with hydrate inhibitor injection.

FIG. 1B is a process flow diagram of a gas conditioning system 168 with hydrate inhibitor injection. Like numbered items are as described with respect to FIG. 1A. The gas conditioning system 168 of FIG. 1B is similar to the gas conditioning system 100 of FIG. 1A. However, the gas conditioning system 168 of FIG. 1B includes two hydrate inhibitor injection units 170 and 172. The hydrate inhibitor injection units 170 and 172 may prevent the formation of hydrates within the gas conditioning system 168, as well as enable the removal of more water and heavy hydrocarbons from the hydrocarbon feed stream 102 upstream of the dehydration unit 162. This may be accomplished without adding heat to the hydrocarbon feed stream 102, and while enabling more refrigeration in the series of conditioning steps. This will, in turn, increase the overall efficiency and operability of the gas conditioning system 168, as well as reduce the capital and operating costs of the gas conditioning system 168.

The hydrate inhibitor injection units 170 and 172 may be configured to inject a hydrate inhibitor into the gas stream flowing through the gas conditioning system 168. The hydrate inhibitor may be any liquid that is capable of lowering the hydrate formation temperature of the gas stream. In various embodiments, the hydrate inhibitor includes MEG, DEG, or TEG, for example. Moreover, the hydrate inhibitor injection units 170 and 172 may include any equipment that is capable of effectively injecting the hydrate inhibitor into the gas stream and mixing the hydrate inhibitor with the gas stream such that the hydrate formation temperature of the gas stream is lowered. For example, in some embodiments, the hydrate inhibitor injection units 170 and 172 may include co-current contactors. In other embodiments, the hydrate inhibitor injection units 170 and 172 include ball misters, static mixers, or simple nozzles or joints between two pipes.

According to embodiments described herein, the first hydrate inhibitor injection unit 170 is located downstream of the slug catcher 104 but upstream of the second pressure reduction unit 134. In various embodiments, the first hydrate inhibitor injection unit 170 is used instead of the inlet gas heater 130 shown in FIG. 1A. The first hydrate inhibitor injection unit 170 may inject the hydrate inhibitor into the gas stream 106 at sufficient volume to lower the hydrate formation temperature of the gas stream 106 and, thus, prevent the formation of hydrates downstream of the second pressure reduction unit 134. The resulting gas stream 174 entering the second pressure reduction unit 134 may be much colder than the heated gas stream 132 entering the second pressure reduction unit 134 in FIG. 1A. As a result, the gas phase stream 136 exiting the second pressure reduction unit 134 may also be much colder than if heat were added to the gas stream 106, as shown in FIG. 1A.

The addition of the first hydrate inhibitor injection unit 170 to the gas conditioning system 168 may help to condense additional heavier hydrocarbons from the gas stream 106 leaving the slug catcher 104. This may mitigate operational problems in the downstream equipment, such as the mercury removal unit 124, the acid gas removal unit 146, and the dehydration unit 162, and increase the total condensate production from a given volume of pipeline outlet fluids. The first hydrate inhibitor injection unit 170 may also help to reduce the temperature of the gas stream feeding the downstream equipment, which may improve the efficiency of the gas conditioning system 168 by reducing the required solvent circulation rate in the acid gas removal unit 146.

Furthermore, in a new facility design, the first hydrate inhibitor injection unit 170 may completely replace the inlet gas heater 130 of FIG. 1A, thus eliminating the need to design, install, and operate the inlet gas heater 130. In an existing facility, the first hydrate inhibitor injection unit 170 may enable operation of the inlet gas heater 130 without any heat input to the gas conditioning system 168, thus reducing the load on the utility system that provides heat to the inlet gas heater 130.

In various embodiments, the hydrate inhibitor injected into the gas stream, as well as the condensed water dissolved in the hydrate inhibitor, is collected in the first separation unit 138 located downstream of the second pressure reduction unit 134. The resulting liquid stream 176 may be sent through the gas/liquid/liquid separation unit 112 and, from there, to a hydrate inhibitor regeneration unit 178. The hydrate inhibitor regeneration unit 178 may be configured to remove the water and other impurities from the hydrate inhibitor, forming a regenerated hydrate inhibitor that may be reused within the hydrate inhibitor injection units 170 and 172.

In various embodiments, the second hydrate inhibitor injection unit 172 is located downstream of the AGRU 146 and upstream of the cooling unit 152. As discussed with respect to FIG. 1A, the sweetened gas stream 150 exiting the AGRU 146 is water saturated. As a result, the sweetened gas stream 150 is typically cooled within the cooling unit 152 to condense the water vapor within the sweetened gas stream 150, reducing the load on the downstream dehydration unit 162. However, the temperature of the process gas stream 154 exiting the cooling unit 152 must be controlled such that the temperature of the process gas stream 154 remains above its hydrate formation temperature of, for example, about 20° C. (68° F.), or higher.

According to embodiments described herein, the second hydrate inhibitor injection unit 172 injects the hydrate inhibitor into the sweetened gas stream 150 at sufficient volume to lower the hydrate formation temperature of the sweetened gas stream 150 and, thus, prevent the formation of hydrates downstream of the cooling unit 152. In various embodiments, the addition of the second hydrate inhibitor injection unit 172 to the gas conditioning system 168 allows the cooling unit 152 to be operated at much lower temperatures, such as −20° C., −40° C., or lower. The lower temperature may help to condense additional water from the gas stream 180 exiting the hydrate inhibitor injection unit 172, thereby reducing the water removal demand on the downstream dehydration unit 162. For embodiments in which the downstream dehydration unit 162 is a molecular sieve unit, the size of the beds within the molecular sieve unit may be reduced in size if the second hydrate inhibitor injection unit 172 is added to a new design. Alternatively, for a fixed molecular sieve bed size within an existing facility, the absorption cycle time may be extended, providing longer bed life by reducing the number of thermal cycles on the molecular sieve material per unit of feed gas. In addition, energy consumption may be reduced by reducing the regeneration time as a percentage of the cycle total. For embodiments in which the dehydration unit 162 employs an alternative dehydration method, such as a triethylene glycol-based dehydration, with or without stripping gas, the reduced water removal load resulting from the use of the second hydrate inhibitor injection unit 172 may reduce the required glycol circulation rate and/or reduce the rate of stripping gas consumption. This may, in turn, reduce the capital and operating costs for the dehydration unit 162.

The second hydrate inhibitor injection unit 172 may also help to condense additional heavy hydrocarbons from the gas stream 180, thus enabling more of the heavy hydrocarbons to be effectively removed from the gas stream 180 upstream of the dehydration unit 162. For embodiments in which the dehydration unit 162 is a molecular sieve unit, this may improve the water removal capacity and extend the life of the molecular sieve material by reducing or eliminating the potential for liquid hydrocarbons to come in contact with the molecular sieve material. Such liquid hydrocarbons can inhibit the ability of the molecular sieve material to adsorb water vapor, and can cause coke formation within the molecular sieve material during a regeneration cycle, which can lead to increased bed pressure drop while in the dehydration portion of the cycle, and can decrease the molecular sieve material's water removal capacity.

In embodiments in which the AGRU 146 removes substantial quantities of $CO_2$ and other contaminants from the gas stream 144, the hydrocarbon dew point of the sweetened gas stream 150 exiting the AGRU 146 may be different from hydrocarbon dew point of the gas stream 144 entering the AGRU 146. Generally, removing $CO_2$ and other contaminants from the gas stream 144 increases the hydrocarbon dew point, increasing the likelihood that the dehydration unit 162 will be exposed to liquid hydrocarbons as a result of retrograde condensation. Therefore, removing more heavy hydrocarbons upstream of the dehydration unit 162 may limit the potential for retrograde condensation in the gas stream upstream of the dehydration unit 162.

Further, in some embodiments, the second hydrate inhibitor injection unit 172 allows for the greater use of a higher-pressure level of refrigerant within the cooling unit 152. This may increase the thermal efficiency of the gas conditioning system 168 by reducing the refrigeration compressor power required to achieve the same level of cooling. Additionally, in some embodiments, the second inhibitor injection unit 172 allows for the use of additional gas chilling units upstream of the dehydration unit 162. The additional gas chilling units may use lower pressure refrigerant to achieve lower gas outlet temperatures.

In various embodiments, the hydrate inhibitor injected into the gas stream, as well as the condensed water dissolved in the hydrate inhibitor, is collected in the second separation unit 156 located downstream of the cooling unit 152. The resulting liquid stream 182 may be sent through the gas/liquid/liquid separation unit 112 and, from there, to the hydrate inhibitor regeneration unit 178. The hydrate inhibitor regeneration unit 178 may be configured to remove the water and other impurities from the hydrate inhibitor, forming a regenerated hydrate inhibitor that may be reused within the hydrate inhibitor injection units 170 and 172.

The process flow diagram of FIG. 1B is not intended to indicate that the gas conditioning system 168 is to include all of the components shown in FIG. 1B. Further, any number of additional components may be included within the gas conditioning system 168, depending on the details of the specific implementation. For example, in some embodiments, additional hydrate inhibitor injection units are added at different locations within the gas conditioning system 168.

Figure 2:
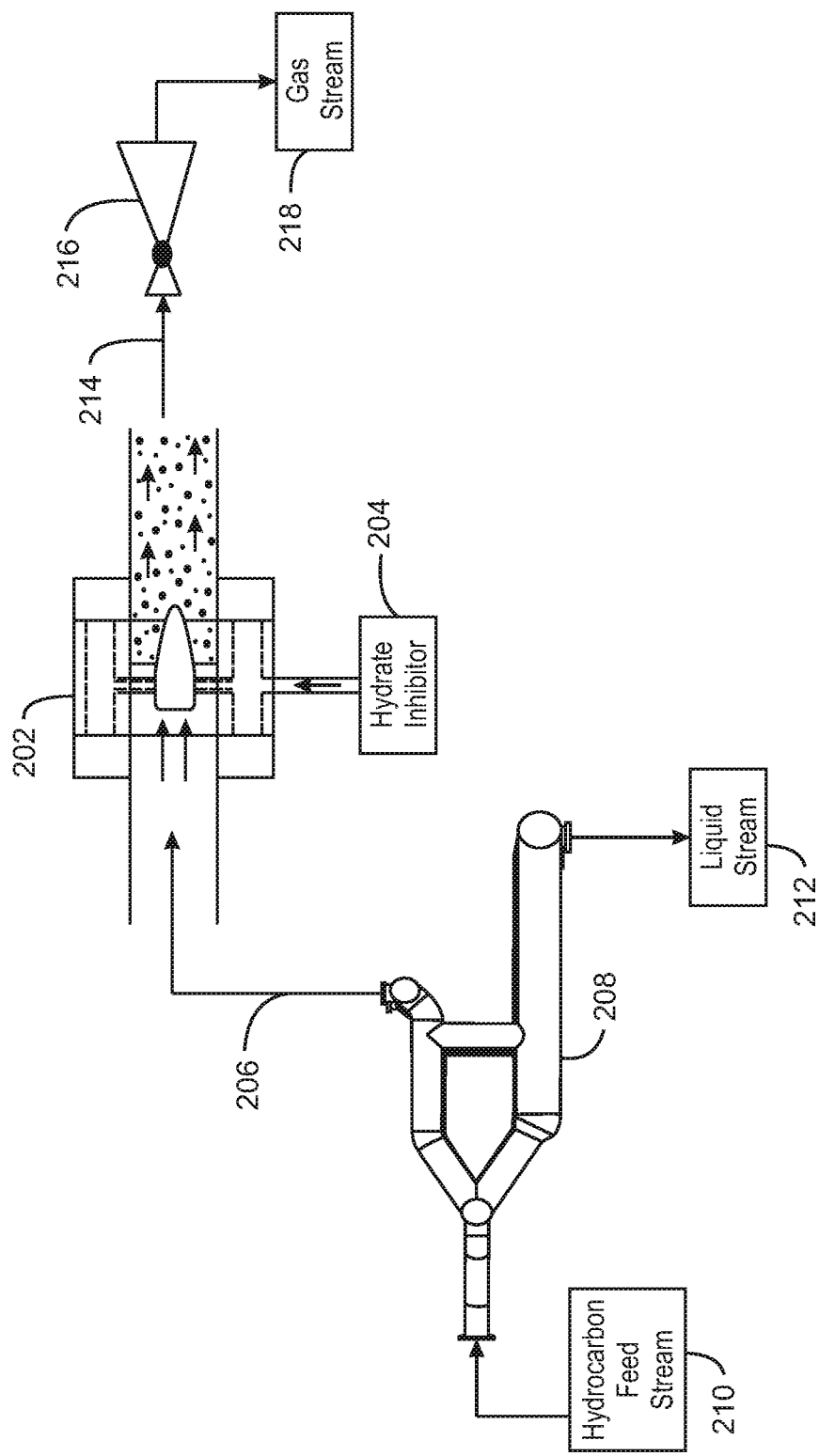
FIG. 2 is a process flow diagram of a portion of a gas conditioning system including hydrate inhibitor injection.

FIG. 2 is a process flow diagram of a portion 200 of a gas conditioning system including hydrate inhibitor injection. In various embodiments, the portion 200 of the gas conditioning system corresponds to the portion of the gas conditioning system 168 of FIG. 1B including the slug catcher 104, the first hydrate inhibitor injection unit 170, and the second pressure reduction unit 134. In the example shown in FIG. 2, the portion 200 of the gas conditioning system includes a co-current contactor 202 for injecting a hydrate inhibitor 204 into a gas stream 206 downstream of a slug catcher 208. Other injection systems may be used instead of the co-current contactor 202, such as a ball mister using a spherical misting head centered in a pipe segment for liquid injection.

In various embodiments, the slug catcher 208 corresponds to the slug catcher 104 described with respect to FIGS. 1A and 1B. Specifically, the slug catcher 208 may separate a hydrocarbon feed stream 210 into the gas stream 206 and a liquid stream 212. In the example shown in FIG. 2, the slug catcher 208 is a finger-type slug catcher including multiple parallel lengths of near-horizontal pipe that are manifolded together and sloped downward from the inlet and again manifolded together at the low elevation point, thereby creating a liquid collection service that can receive and contain the liquid slugs. In some examples, the slug catcher is a settling tank. The liquid inventory thereby contained in the slug catcher can then be processed at a relatively constant rate. The slug catcher 208 may also be designed to facilitate gas disengagement from the liquids through another set of piping manifolds located on the inlet end and the top of the slug catcher 208, and produce a relatively constant rate of gas flow to downstream equipment.

From the slug catcher 208, the gas stream 206 may flow into the co-current contactor 202. In various embodiments, the co-current contactor 202 corresponds to the first hydrate inhibitor injection unit 170 described with respect to FIG. 1B. The co-current contactor 202 may be configured to allow the gas stream 206 and the hydrate inhibitor 204 to co-currently flow into the co-current contactor 202. The co-current contactor 202 may provide for the efficient incorporation of liquid droplets formed from the hydrate inhibitor 204 into the gas stream 206. This may, in turn, alter the hydrate formation temperature of the gas stream 206 from an initial hydrate formation temperature to a lowered hydrate formation temperature, thus helping to prevent the formation of hydrates within the gas conditioning system.

The resulting gas stream 214 exiting the co-current contactor 202 may then be flowed through a pressure-reducing control valve 216. In various embodiments, the pressure-reducing control valve 216 corresponds to the second pressure reduction unit 134 of FIGS. 1A and 1B. The gas stream 218 exiting the pressure-reducing control valve 216 may then be flowed to the next stage of the gas conditioning system, such as, for example, a separation unit (not shown).

The process flow diagram of FIG. 2 is not intended to indicate that the portion 200 of the gas conditioning system is to include all of the components shown in FIG. 2. Further, any number of additional components may be included within the portion 200 of the gas conditioning system, depending on the details of the specific implementation.

Figure 3:
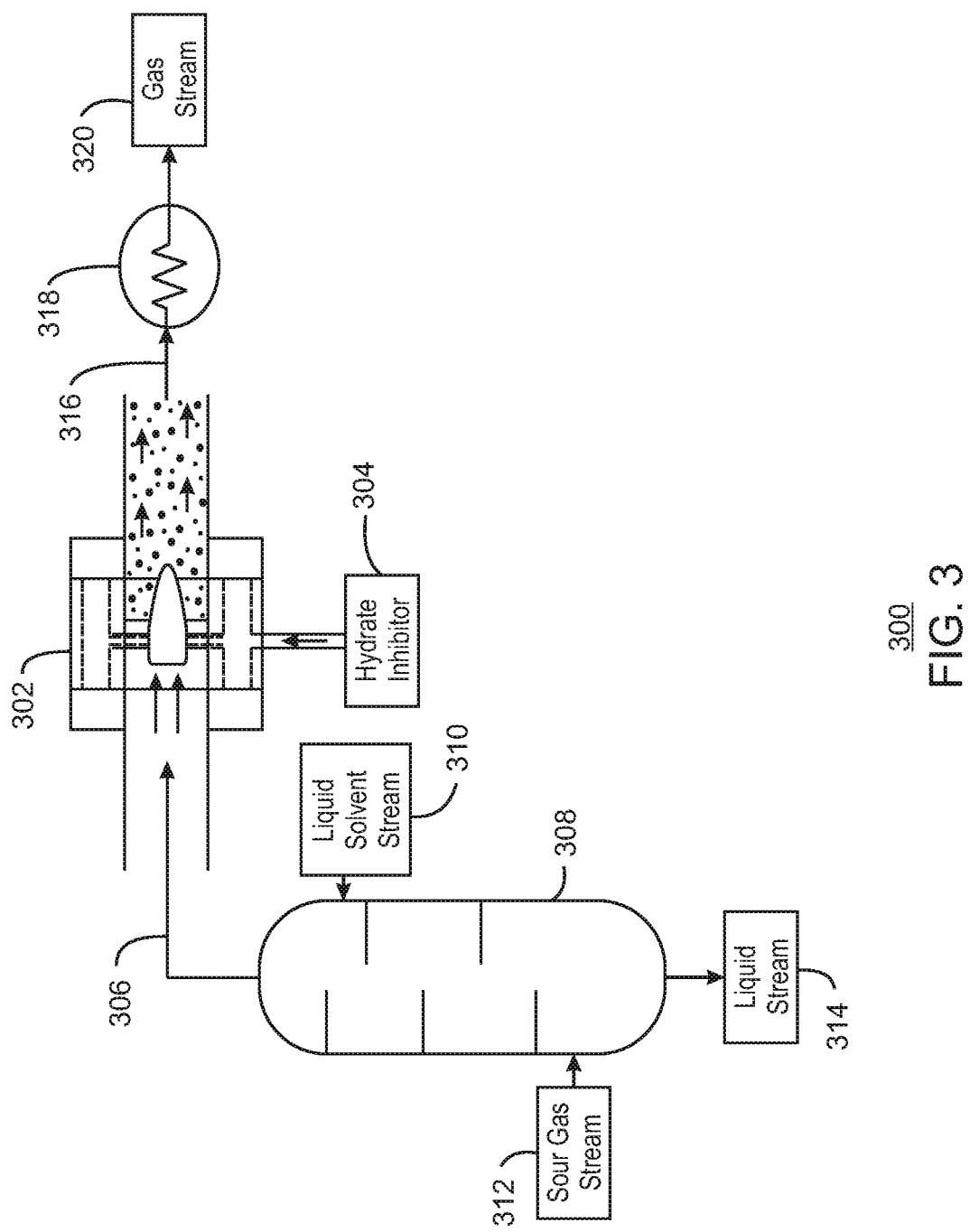
FIG. 3 is a process flow diagram of another portion of a gas conditioning system including hydrate inhibitor injection.

FIG. 3 is a process flow diagram of another portion 300 of a gas conditioning system including hydrate inhibitor injection. In various embodiments, the portion 300 of the gas conditioning system shown in FIG. 3 corresponds to the portion of the gas conditioning system 168 of FIG. 1B including the AGRU 146, the second hydrate inhibitor injection unit 172, and the cooling unit 152. As shown in FIG. 3, the portion 300 of the gas conditioning system may include a co-current contactor 302 for injecting a hydrate inhibitor 304 into a gas stream 306 downstream of an acid gas removal column 308.

In various embodiments, the acid gas removal column 308 corresponds to the AGRU 146 described with respect to FIGS. 1A and 1B. According to the embodiment shown in FIG. 3, the acid gas removal column 308 is a conventional absorber column that employs a counter-current flow scheme. Specifically, a liquid solvent stream 310 may be injected into the top of the acid gas removal column 308, while a sour gas stream 312 may be flowed into the bottom of the acid gas removal column 308. As the sour gas stream 312 flows upward through the falling liquid solvent stream 310, the acid gases within the sour gas stream 312 are absorbed by the liquid solvent stream 310, producing the sweetened gas stream 306 and a liquid stream 314 including the absorbed acid gases.

The sweetened gas stream 306 may then be flowed into the co-current contactor 302. In various embodiments, the co-current contactor 302 may correspond to the second hydrate inhibitor injection unit 172 described with respect to FIG. 1B. The co-current contactor 302 may be configured to allow the sweetened gas stream 306 and the hydrate inhibitor 304 to co-currently flow into the co-current contactor 302. The co-current contactor 302 may provide for the efficient incorporation of liquid droplets formed from the hydrate inhibitor 304 into the gas stream 306. This may, in turn, alter the hydrate formation temperature of the gas stream 306 from an initial hydrate formation temperature to a lowered hydrate formation temperature, thus helping to prevent the formation of hydrates within the gas conditioning system.

The resulting gas stream 316 exiting the co-current contactor 302 may then be flowed through a heat exchanger 318. In various embodiments, the heat exchanger 318 may correspond to the cooling unit 152 of FIGS. 1A and 1B. The gas stream 320 exiting the heat exchanger 318 may then be flowed to the next stage of the gas conditioning system, such as, for example, a separation unit (not shown).

The process flow diagram of FIG. 3 is not intended to indicate that the portion 300 of the gas conditioning system is to include all of the components shown in FIG. 3. Further, any number of additional components may be included within the portion 300 of the gas conditioning system, depending on the details of the specific implementation. For example, in some embodiments, a series of heat exchangers may be included within the portion 300 of the gas conditioning system instead of the single heat exchanger 318 shown in FIG. 3.

Figure 4:
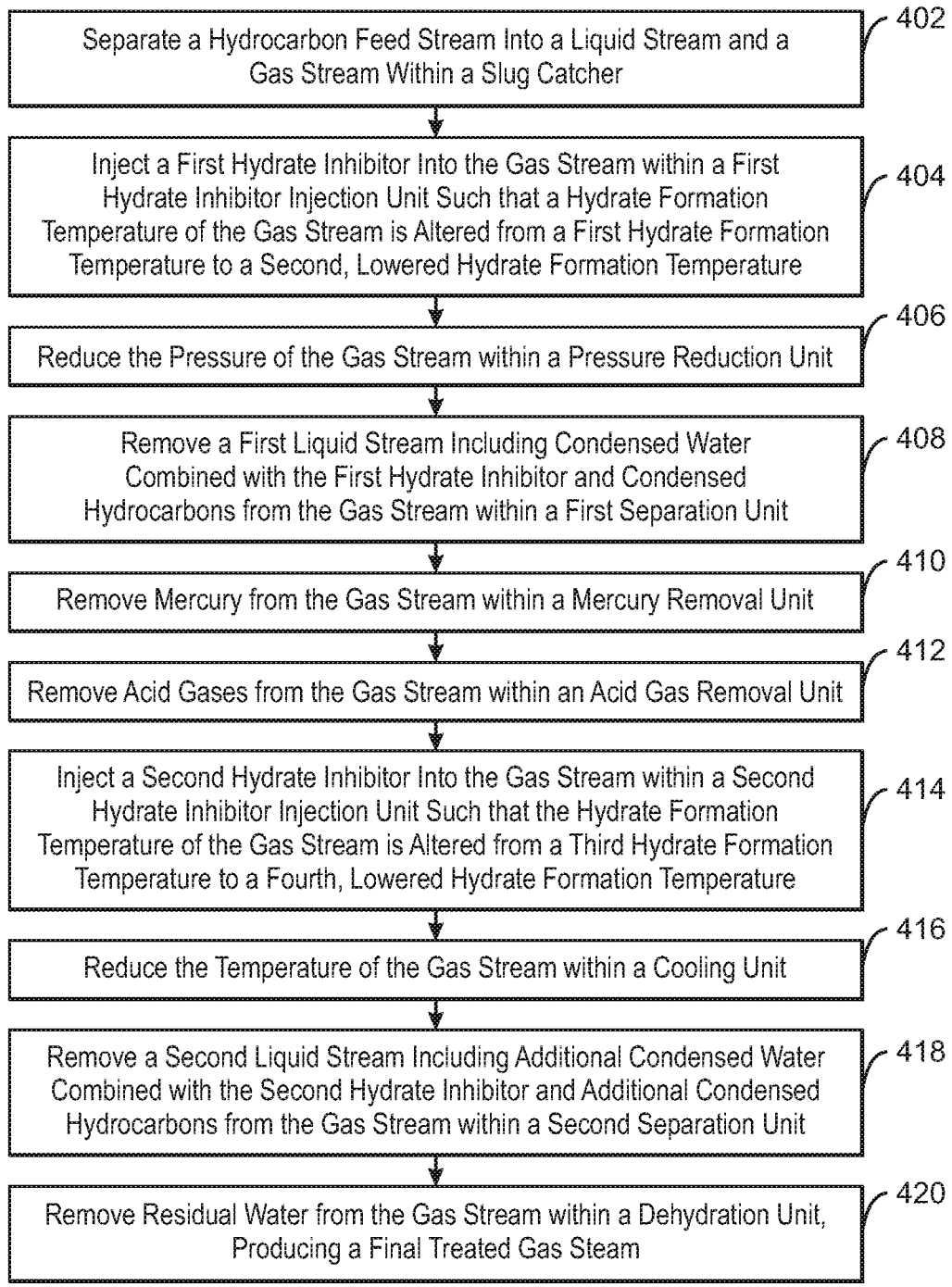
FIG. 4 is a process flow diagram of a method for improving the efficiency of a gas conditioning system via hydrate inhibitor injection.

Methods for Improving the Efficiency of a Gas Conditioning System Via Hydrate Inhibitor Injection FIG. 4 is a process flow diagram of a method 400 for improving the efficiency of a gas conditioning system via hydrate inhibitor injection. In various embodiments, the method 400 is implemented by a gas conditioning system, such as the gas conditioning system 168 described with respect to FIG. 1B. The method 400 begins at block 402, at which a hydrocarbon feed stream is separated into a liquid stream and a gas stream within a slug catcher. The slug catcher may correspond to the slug catchers 104 and 208 described with respect to FIGS. 1A, 1B, and 2. Moreover, in some embodiments, the hydrocarbon feed stream may be separated into two liquid streams and the gas stream within the slug catcher, as described with respect to FIG. 1A.

At block 404, a first hydrate inhibitor is injected into the gas stream within a first hydrate inhibitor injection unit such that the hydrate formation temperature of the gas stream is altered from a first hydrate formation temperature to a second, lowered hydrate formation temperature. The first hydrate inhibitor injection unit may correspond to the first hydrate inhibitor injection unit 170 of FIG. 1B and/or the co-current contactor 202 of FIG. 2. In various embodiments, lowering the hydrate formation temperature of the gas stream helps to ensure that hydrates do not form when the gas stream flows through a pressure reduction unit, as described with respect to block 406.

According to embodiments described herein, the first hydrate inhibitor injection unit may include a co-current contactor, a ball mister, a static mixer, a spray nozzle, or any other equipment that is capable of efficiently mixing the hydrate inhibitor with the gas stream. Moreover, the first hydrate inhibitor may be MEG, DEG, or TEG, for example.

At block 406, the pressure of the gas stream is reduced within the pressure reduction unit. The pressure reduction unit may correspond to the second pressure reduction unit 134 described with respect to FIGS. 1A and 1B, and/or the pressure-reducing control valve 216 described with respect to FIG. 2.

At block 408, a first liquid stream including condensed water combined with the first hydrate inhibitor and condensed hydrocarbons is separated from the gas stream within a first separation unit. In some embodiments, the first separation unit may correspond to the first separation unit 138 described with respect to FIGS. 1A and 1B.

At block 410, mercury is removed from the gas stream within a mercury removal unit. In various embodiments, the mercury removal unit corresponds to the mercury removal unit 124 described with respect to FIGS. 1A and 1B.

At block 412, acid gases are removed from the gas stream within an acid gas removal unit. The acid gas removal unit may correspond to the acid gas removal unit 146 of FIGS. 1A and 1B and/or the acid gas removal column 308 of FIG. 3.

At block 414, a second hydrate inhibitor is injected into the gas stream within a second hydrate inhibitor injection unit such that the hydrate formation temperature of the gas stream is altered from a third hydrate formation temperature to a fourth, lowered hydrate formation temperature. The second hydrate inhibitor injection unit may correspond to the second hydrate inhibitor injection unit 172 of FIG. 1B and/or the co-current contactor 302 of FIG. 3. In various embodiments, lowering the hydrate formation temperature of the gas stream helps to ensure that hydrates do not form when the gas stream flows through a cooling unit, as described with respect to block 416.

According to embodiments described herein, the second hydrate inhibitor injection unit may include a co-current contactor, a ball mister, a static mixer, a spray nozzle, or any other equipment that is capable of efficiently mixing the hydrate inhibitor with the gas stream. Moreover, the second hydrate inhibitor may be MEG, DEG, or TEG, for example.

At block 416, the temperature of the gas stream is reduced within a cooling unit. In various embodiments, the cooling unit corresponds to the cooling unit 152 of FIGS. 1A and 1B and/or the heat exchanger 318 of FIG. 3.

At block 418, a second liquid stream including additional condensed water combined with the second hydrate inhibitor and additional condensed hydrocarbons is removed from the gas stream within a second separation unit. The second separation unit may correspond to the second separation unit 156 described with respect to FIGS. 1A and 1B.

At block 420, residual water is removed from the gas stream within a dehydration unit, producing a final treated gas stream. The dehydration unit may correspond to the dehydration unit 162 described with respect to FIGS. 1A and 1B. In some embodiments, the final treated gas stream is sent to a gas processing facility located downstream of the gas conditioning system, and LNG is produced and/or NGLs are recovered from the final treated gas stream within the gas processing facility.

The process flow diagram of FIG. 4 is not intended to indicate that the steps of the method 400 are to be executed in any particular order, or that all of the steps of the method 400 are to be included in every case. Further, any number of additional steps not shown in FIG. 4 may be included within the method 400, depending on the details of the specific implementation. For example, in some embodiments, the first liquid stream and the second liquid stream are separated into a liquid hydrocarbon stream including the condensed hydrocarbons and the additional condensed hydrocarbons, a rich hydrate inhibitor stream including the first hydrate inhibitor, the second hydrate inhibitor, the condensed water, and the additional condensed water, and a first off gas stream within a gas/liquid/liquid separation unit. A regenerated hydrate inhibitor stream is then produced from the rich hydrate inhibitor stream within a hydrate inhibitor regeneration unit, and at least a portion of the regenerated hydrate inhibitor stream is reused within the first hydrate inhibitor injection unit and the second hydrate inhibitor injection unit. Moreover, the liquid hydrocarbon stream is separated into a second off gas stream and a liquid stream including field condensate within a condensate stabilizer. The first off gas stream and the second off gas stream are then flowed back into the gas conditioning system upstream of the mercury removal unit.

Figure 5:
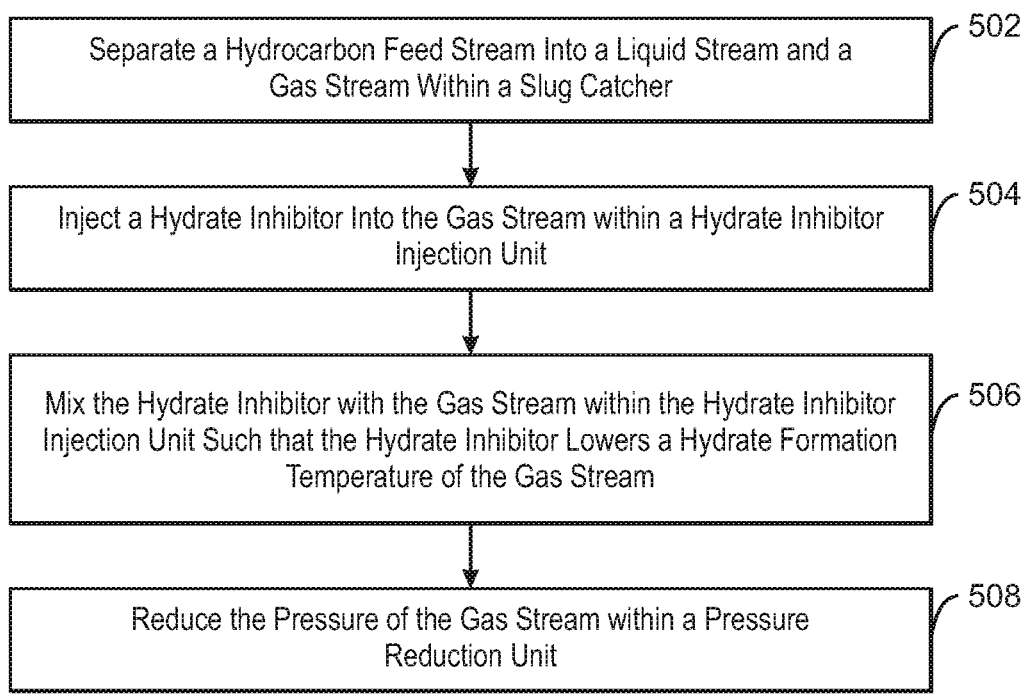
FIG. 5 is a process flow diagram of a method for injecting a hydrate inhibitor into a gas stream prior to reducing the pressure of the gas stream.

FIG. 5 is a process flow diagram of a method 500 for injecting a hydrate inhibitor into a gas stream prior to reducing the pressure of the gas stream. In various embodiments, the method 500 is implemented by a gas conditioning system, such as the gas conditioning system 168 described with respect to FIG. 1B. Moreover, in some embodiments, the method 500 is implemented by the portion 200 of the gas conditioning system described with respect to FIG. 2.

The method 500 begins at block 502, at which a hydrocarbon feed stream is separated into a liquid stream and a gas stream within a slug catcher. At block 504, a hydrate inhibitor is injected into the gas stream within a hydrate inhibitor injection unit. At block 506, the hydrate inhibitor is mixed with the gas stream within the hydrate inhibitor injection unit such that the hydrate inhibitor lowers the hydrate formation temperature of the gas stream. Finally, at block 508, the pressure of the gas stream is reduced within a pressure reduction unit.

The process flow diagram of FIG. 5 is not intended to indicate that the steps of the method 500 are to be executed in any particular order, or that all of the steps of the method 500 are to be included in every case. Further, any number of additional steps not shown in FIG. 5 may be included within the method 500, depending on the details of the specific implementation.

Figure 6:
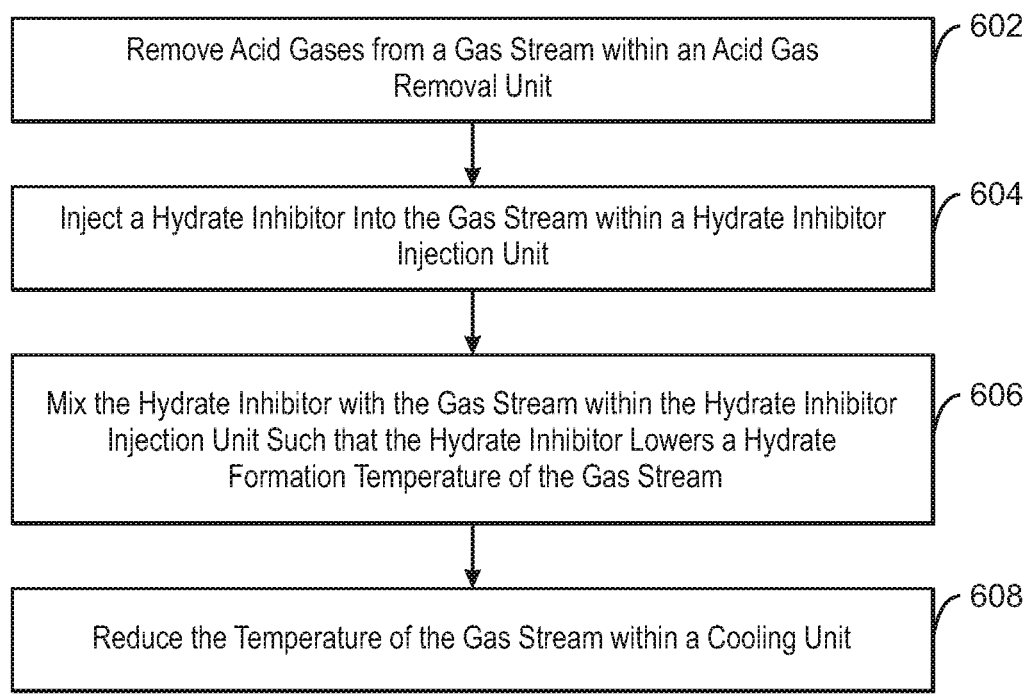
FIG. 6 is a process flow diagram of a method for injecting a hydrate inhibitor into a gas stream prior to reducing the temperature of the gas stream.

FIG. 6 is a process flow diagram of a method 600 for injecting a hydrate inhibitor into a gas stream prior to reducing the temperature of the gas stream. In various embodiments, the method 600 is implemented by a gas conditioning system, such as the gas conditioning system 168 described with respect to FIG. 1B. Moreover, in some embodiments, the method 600 is implemented by the portion 300 of the gas conditioning system described with respect to FIG. 3.

The method 600 begins at block 602, at which acid gases are removed from a gas stream within an acid gas removal unit. At block 604, a hydrate inhibitor is injected into the gas stream within a hydrate inhibitor injection unit. At block 606, the hydrate inhibitor is mixed with the gas stream within the hydrate inhibitor injection unit such that the hydrate inhibitor lowers the hydrate formation temperature of the gas stream. At block 608, the temperature of the gas stream is reduced within a cooling unit.

The process flow diagram of FIG. 6 is not intended to indicate that the steps of the method 600 are to be executed in any particular order, or that all of the steps of the method 600 are to be included in every case. Further, any number of additional steps not shown in FIG. 6 may be included within the method 600, depending on the details of the specific implementation.

While the present techniques may be susceptible to various modifications and alternative forms, the embodiments discussed above have been shown only by way of example. However, it should again be understood that the techniques are not intended to be limited to the particular embodiments disclosed herein. Indeed, the present techniques include all alternatives, modifications, and equivalents falling within the true spirit and scope of the appended claims.

What is claimed is:

1. A method for improving the efficiency of a gas conditioning system via hydrate inhibitor injection, comprising:
    separating a hydrocarbon feed stream into a liquid stream and a first gas stream within a slug catcher;
    injecting a first hydrate inhibitor into the first gas stream within a first hydrate inhibitor injection unit, thereby producing a second gas stream of the first gas stream and the first hydrate inhibitor, such that a hydrate formation temperature of the first gas stream is altered from a first hydrate formation temperature to a second, lowered hydrate formation temperature for the second gas stream;
    reducing a pressure of the second gas stream within a pressure reduction unit, thereby producing a third gas stream, and transporting the third gas stream from the pressure reduction unit to a first separation unit;
    removing a first liquid stream comprising condensed water combined with the first hydrate inhibitor and condensed hydrocarbons from the third gas stream within the first separation unit, thereby producing a fourth gas stream, and transporting the fourth gas stream to a mercury removal unit;
    removing mercury from the fourth gas stream within the mercury removal unit, thereby producing a fifth gas stream, and transporting fifth the gas stream to an acid gas removal unit;
    removing acid gases from the fifth gas stream within the acid gas removal unit, thereby producing a sixth gas stream, and transporting the sixth gas stream to a second hydrate inhibitor injection unit;
    injecting a second hydrate inhibitor into the sixth gas stream within the second hydrate inhibitor injection unit, thereby producing a seventh gas stream, such that the hydrate formation temperature of the sixth gas stream is altered from a third hydrate formation temperature to a fourth, lowered hydrate formation temperature for the seventh gas stream, and transporting the seventh gas stream to a cooling unit;
    reducing a temperature of the seventh gas stream within the cooling unit, thereby obtaining an eighth gas stream, and transporting the eighth gas stream to a second separation unit;
    removing a second liquid stream comprising additional condensed water combined with the second hydrate inhibitor and additional condensed hydrocarbons from the eighth gas stream within the second separation unit, thereby producing a ninth gas stream, and transporting the ninth gas stream to a dehydration unit; and
    removing residual water from the ninth gas stream within the dehydration unit, producing a final treated gas stream.

2. The method of claim 1, comprising:
    transporting the first liquid stream and the second liquid stream to a gas/liquid/liquid separation unit;

separating the first liquid stream and the second liquid stream into (i) a liquid hydrocarbon stream comprising the condensed hydrocarbons and the additional condensed hydrocarbons, (ii) a rich hydrate inhibitor stream comprising the first hydrate inhibitor, the second hydrate inhibitor, the condensed water, and the additional condensed water, and (iii) a first off gas stream within the gas/liquid/liquid separation unit;

transporting the rich hydrate inhibitor stream to a hydrate inhibitor regeneration unit; and producing a regenerated hydrate inhibitor stream from the rich hydrate inhibitor stream within the hydrate inhibitor regeneration unit; and reusing at least a portion of the regenerated hydrate inhibitor stream within the first hydrate inhibitor injection unit and the second hydrate inhibitor injection unit.

3. The method of claim 2, comprising:

transporting the liquid hydrocarbon stream to a condensate stabilizer;

separating the liquid hydrocarbon stream into a second off gas stream and a liquid stream comprising field condensate within the condensate stabilizer; and flowing the first off gas stream and the second off gas stream back into the gas conditioning system upstream of the mercury removal unit.

4. The method of claim 1, wherein the first hydrate inhibitor and the second hydrate inhibitor comprise monoethylene glycol (MEG), diethylene glycol (DEG), or triethylene glycol (TEG).

5. The method of claim 1, wherein the first hydrate inhibitor injection unit and the second hydrate inhibitor injection unit comprise co-current contactors, ball misters, static mixers, or spray nozzles.

6. The method of claim 1, comprising: flowing the final treated gas stream to a gas processing facility located downstream of the gas conditioning system; and producing LNG or recovering NGLs from the final treated gas stream within the gas processing facility.

\* \* \* \* \*